(12) United States Patent
Kuusela et al.

(10) Patent No.: US 10,850,129 B2
(45) Date of Patent: *Dec. 1, 2020

(54) DOSE-DISTRIBUTION ESTIMATION IN PROTON THERAPY

(71) Applicant: Varian Medical Systems International AG., Cham (CH)

(72) Inventors: Esa Kuusela, Espoo (FI); Maria Cordero Marcos, Espoo (FI); Janne Nord, Espoo (FI)

(73) Assignee: Varian Medical Systems International, AG., Cham (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/231,045

(22) Filed: Dec. 21, 2018

(65) Prior Publication Data

US 2019/0134427 A1 May 9, 2019

Related U.S. Application Data

(63) Continuation of application No. 15/085,804, filed on Mar. 30, 2016, now Pat. No. 10,159,853.

(51) Int. Cl.
*A61N 5/10* (2006.01)

(52) U.S. Cl.
CPC .......... *A61N 5/1071* (2013.01); *A61N 5/103* (2013.01); *A61N 5/1031* (2013.01); *A61N 2005/1041* (2013.01); *A61N 2005/1087* (2013.01)

(58) Field of Classification Search
CPC .................. A61N 5/1071; A61N 2005/1087
See application file for complete search history.

(56) References Cited

U.S. PATENT DOCUMENTS

| | | | |
|---|---|---|---|
| 8,644,571 B1 | 2/2014 | Schulte et al. | |
| 10,159,853 B2 * | 12/2018 | Kuusela | A61N 5/1071 |

FOREIGN PATENT DOCUMENTS

| | | |
|---|---|---|
| WO | 2011053802 | 5/2011 |
| WO | 2011153639 | 12/2011 |
| WO | 2013180969 | 12/2013 |
| WO | 2017044562 | 3/2017 |

* cited by examiner

*Primary Examiner* — Kyoung Lee

(57) ABSTRACT

A system for estimating a dose from a proton therapy plan includes a memory that stores machine instructions and a processor coupled to the memory that executes the machine instructions to subdivide a representation of a volume of interest in a patient anatomy traversed by a planned proton field into a plurality of voxels. The processor further executes the machine instructions to determine the distance from the source of the planned proton beam to one of the voxels. The processor also executes the machine instructions to compute the discrete contribution at the voxel to an estimated dose received by the volume of interest from the planned proton beam based on the distance between the source and the volume of interest.

20 Claims, 5 Drawing Sheets

DOSE-DISTRIBUTION ESTIMATION IN PROTON THERAPY

CROSS REFERENCE TO RELATED APPLICATIONS

This application is related to concurrently filed patent application Ser. No. 15/085,804, entitled "DOSE-DISTRIBUTION ESTIMATION IN PROTON THERAPY,", having a filing date of Mar. 30, 2016, which is herein incorporated by reference in its entirety.

TECHNICAL FIELD

This description relates generally to radiation therapy, and more particularly to proton beam therapy treatment plan development.

BACKGROUND

Radiation therapy treatment plan development generally employs medical imaging, such as X-ray, computed tomography (CT), magnetic resonance imaging (MRI), or the like. Typically, a series of two-dimensional patient images, each representing a two-dimensional cross-sectional "slice" of the patient anatomy, are used to reconstruct a three-dimensional representation of a volume of interest (VOI), or structure of interest, from the patient anatomy. The VOI typically includes one or more organs of interest, often including a planning target volume (PTV), such as a malignant growth or an organ including malignant tissue targeted for radiation therapy; a relatively healthy organ at risk (OAR) in the vicinity of a malignant growth at risk of radiation therapy exposure; or a larger portion of the patient anatomy that includes a combination of one or more PTVs along with one or more OARs. The objective of the radiation therapy treatment plan development typically aims to irradiate as much of the PTV as near the prescription dose as possible, while attempting to minimize irradiation of nearby OARs.

The resulting radiation therapy treatment plans are used during medical procedures to selectively expose precise areas of the body, such as malignant tumors, to specific doses of radiation in order to destroy the undesirable tissues. During the development of a patient-specific radiation therapy treatment plan, information generally is extracted from the three-dimensional model to determine parameters such as the shape, volume, location, and orientation of one or more PTVs along with one or more OARs.

Proton beam therapy permits relatively fine control regarding the three-dimensional concentration of energy release from the proton beam within the patient. In particular, the depth dose curve of proton beams has unique characteristics with regard to other types of radiation, such as electron, X-ray or photon beams. As a result, existing treatment plan development methodologies, such as those based on typical photon depth dose curves, may not accurately predict the results that may be achieved with proton beam therapy.

SUMMARY

According to one embodiment of the present invention, a system for estimating a dose from a proton therapy plan includes a memory that stores machine instructions and a processor coupled to the memory that executes the machine instructions to subdivide a representation of a volume of interest into a first plurality of voxels. The processor further executes the machine instructions to determine a first distance associated with a first planned proton field and a first voxel of the first plurality of voxels. The processor also executes the machine instructions to compute a metric based on the first distance and a second distance associated with a target volume traversed by the first planned proton field.

According to another embodiment of the present invention, a computer-implemented method of estimating a dose from a proton therapy plan includes subdividing a representation of a volume of interest into a first plurality of voxels, and determining a first distance associated with a first planned proton field and a first voxel of the first plurality of voxels. The method further includes computing a metric based on the first distance and a second distance associated with a target volume traversed by the first planned proton field.

According to yet another embodiment of the present invention, a computer program product for estimating a dose from a proton therapy plan includes a non-transitory, computer-readable storage medium encoded with instructions adapted to be executed by a processor to implement subdividing a representation of a volume of interest into a first plurality of voxels. The instructions are further adapted to implement determining a first distance associated with a first planned proton field and a first voxel of the first plurality of voxels. The instructions are also adapted to implement computing a metric based on the first distance and a second distance associated with a target volume traversed by the first planned proton field. The metric represents a discrete contribution at the first voxel to an estimated dose received by the volume of interest.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
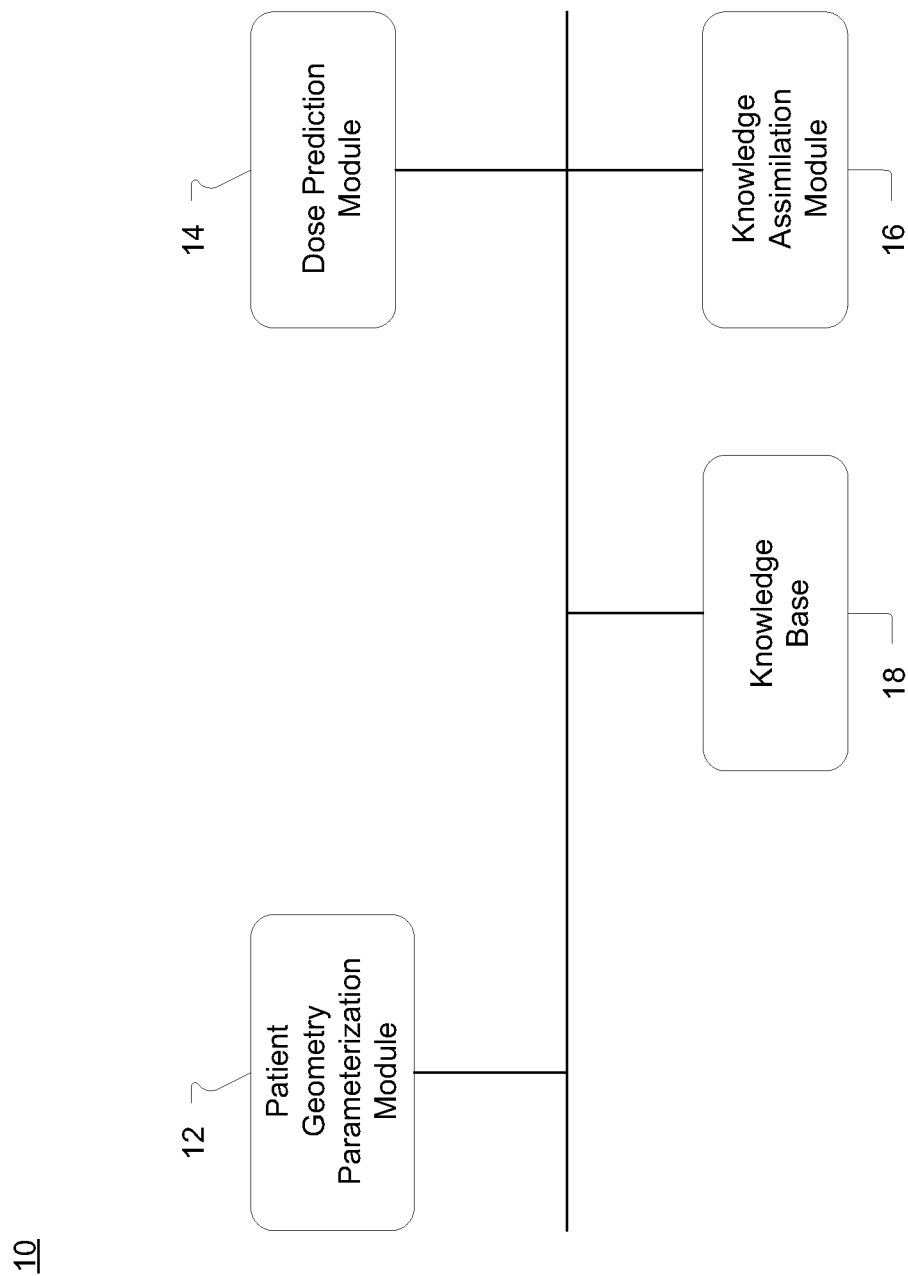
FIG. 1 is a block diagram illustrating an exemplary proton beam dose distribution planning tool that employs a proton geometry-expected-dose to develop and evaluate patient-specific proton therapy treatment plans in accordance with an embodiment of the present invention.

An embodiment of the present invention is shown in FIG. 1, which illustrates an exemplary proton beam dose distribution planning tool 10 that employs a proton beam geometry-expected-dose (GED) to develop and evaluate patient-specific proton therapy treatment plans. The proton beam dose distribution planning tool 10 predicts the dose received by a volume of interest, such as a target volume, during a proton beam therapy session. The proton beam dose distribution planning tool 10 predicts the three-dimensional dose distribution for a new patient based on the patient anatomy and the proton field geometry.

The proton beam dose distribution planning tool 10 includes a patient geometry parametrization module 12, a dose prediction module 14, a knowledge assimilation module 16 and a knowledge base 18. The patient geometry parametrization module 12 generates a set of parameters, or metrics, based on the individual patient anatomic geometry with respect to various factors that affect proton beam dose distribution. Various patient geometric features can affect proton beam dose distribution. Metrics that take into account these geometric features offer relatively improved correlation between predicted proton beam dose distribution and structure positions in patient geometry.

Figure 2:
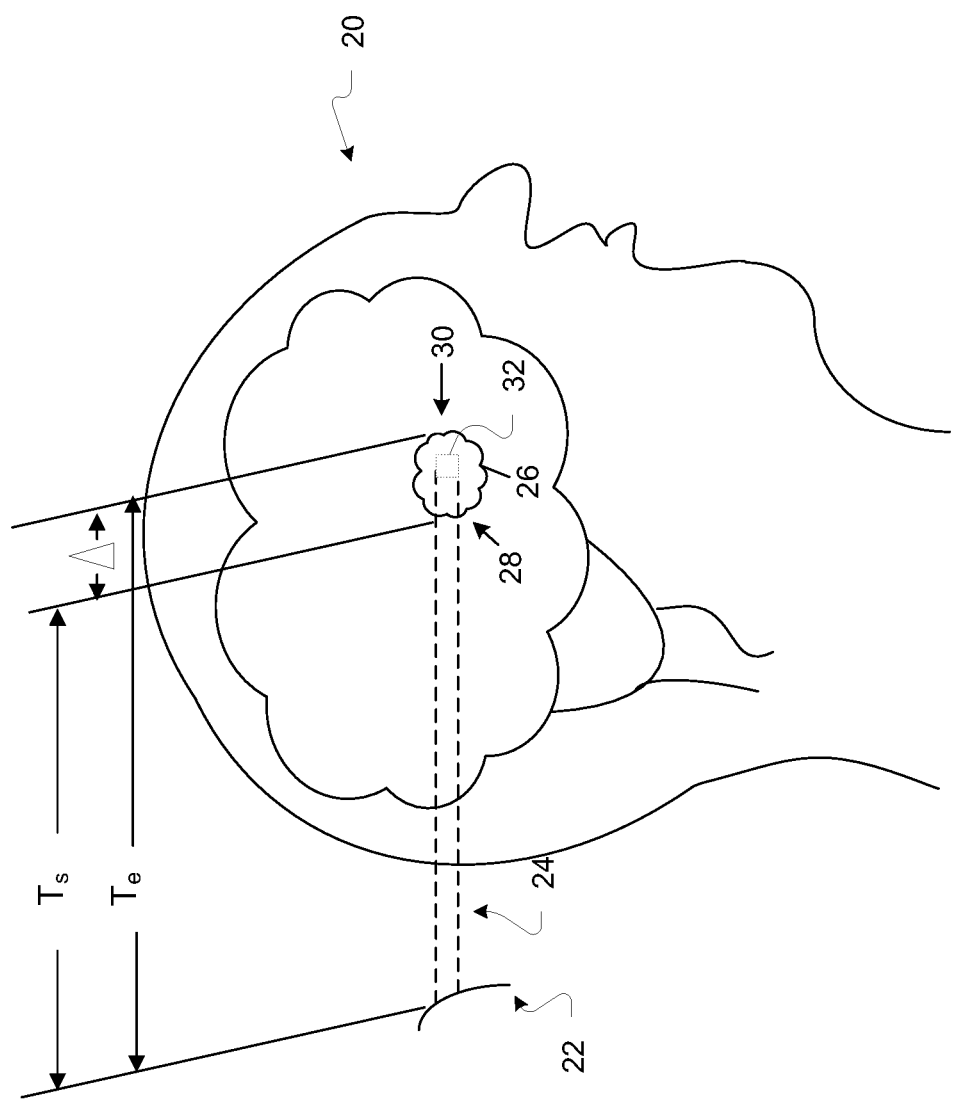
FIG. 2 is an illustration of an exemplary radiation therapy patient anatomy that can be evaluated using the proton beam dose distribution planning tool of FIG. 1.

Referring to FIG. 2, an illustration is shown of an exemplary radiation therapy patient anatomy 20 that can be evaluated using the proton beam dose distribution planning tool 10 of FIG. 1. A proton source 22 emits a proton beam or field 24 toward a target volume 26 in the patient anatomy 20. The proton field 24 enters the proximal boundary 28 of the target volume 26 at distance $T_s$ from the proton source 22 and reaches the distal boundary 30 of the target volume 26 at distance $T_e$ from the proton source 22. The proton field 24 travels distance $\Delta$ through the target volume 26.

The patient geometry parametrization module 12 of FIG. 1 determines a set of parameters, or metrics, to represent the patient anatomy 20 of FIG. 2. In an embodiment, the patient anatomy 20 may be subdivided into a number of individual volume partitions, or voxels, such as exemplary voxel 32, that are individually evaluated with regard to dose distribution. Metrics may be assigned to each voxel based, for example, on the distance from each field origin to the voxel, the prescription dose of the target volume 26, and field parameters based on the planned proton field. The metrics may take into account the field position and orientation.

Examples of expected dose metrics in addition to organ at risk (OAR)-target proximity include but are not limited to the volume of the target structure, the volume of the OAR, any portion of the OAR that is not located within the field of the proton beam, the number and orientation of applied proton beam fields, field geometry, target and OAR tissue densities, the prescription dose, and the like. For example, various metrics can take into account the number of fields that converge at each point in the patient geometry, or any organ passed through by a field before reaching the target volume. Additional metrics can account for tissue characteristics, for example, the Hounsfield unit (HU) scale can represent energy deposition and dispersion characteristics.

For example, the dose attenuation, or fall-off, profile is not symmetric, but rather, drops off much more rapidly as location extends beyond the vicinity of the target volume toward an out-of-field region. In addition, application of multiple fields with differing target dose levels at varying distances from a point in an OAR further complicate the determination of an equivalent distance using combined metrics.

An embodiment of the present invention generates metrics with respect to the target volume and OARs based on a geometrically-expectable dose (GED) distribution. GED metrics incorporate general assumptions regarding how a clinical dose delivery is organized with respect to the target shape. GED metrics also take into account the geometry of the field setup. The dose at any point in an OAR is equal to the sum of the individual contributory doses at that location, or voxel, due to each of the applied target-level fields.

In an embodiment, OAR geometry is included in GED metrics, for example, the number of voxels in OARs that are crossed by a field before reaching the target volume. In another embodiment, conformal dose metrics are employed, including descriptive setup and patient geometry factors. The beam orientation module 14 evaluates the patient geometry metrics and determines preferred beam geometry in the form of one or more beam orientations that meet the constraints for the target volume and OARs.

In an embodiment, the field intensity is modulated to tailor the dose distribution to the specific target form. Target anatomical features, including, for example, the shape, elongation, and position of the target with respect to multiple fields, preferred directions, or beam orientations, are defined. Thus, for example, fields that are perpendicular to the target main direction are allowed to deliver less energy than fields that are parallel to the target main direction.

Further, in an embodiment, the energy level delivered across a field is modulated with respect to GED metrics assigned to each beamlet within a field. For example, metrics can be defined regarding the number of voxels the beamlet crosses, or the distance the beamlet travels through the patient before reaching the target volume, and the intensity of the beamlet can be adjusted according to the metrics.

The dose prediction module 14 evaluates the proton beam dose distribution with respect to a specific set of metrics and a specific grouping of proton beam orientations. The dose prediction module 14 employs a knowledge-based proton dose prediction algorithm that predicts the viable proton beam dose distribution on a structure of interest based on a set of anatomical features. The proton dose prediction algorithm estimates the quality of treatment plan achieved based on detailed planning for specific target geometries and field geometries.

Figure 3:
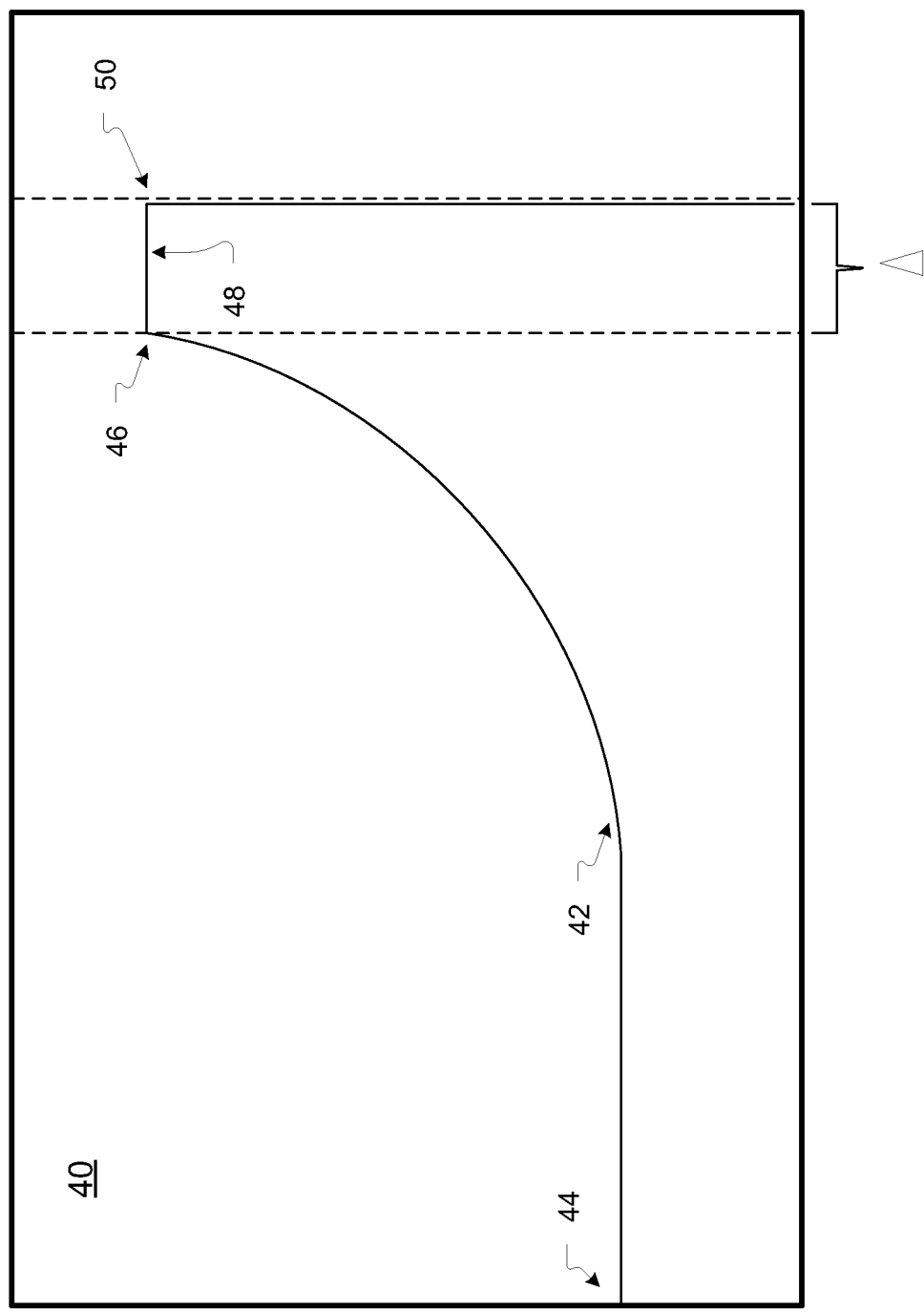
FIG. 3 is graph depicting exemplary proton beam depth dose curve that can be implemented using the proton beam dose distribution planning tool of FIG. 1.

In particular, the dose prediction module 14 creates and applies proton-specific dose-volume histogram (DVH) estimation models. The dose prediction module 14 takes into account the characteristics of the proton beam in order to evaluate the field geometry. Referring to FIG. 3, a graph 40 depicts an exemplary proton beam depth dose curve 42 that can be used by the dose prediction module 14 to create a DVH estimation model. In an embodiment, the depth dose curve 42 represents the approximate dose distribution under the assumption of uniform target dose coverage from each beam.

According to the depth dose curve 42, the amount of energy released by the proton beam along its path increases exponentially from the proton beam source 44 to the point where the proton beam enters the target volume, $T_s$, 46. In addition, according to the dose curve 42, the dose delivered by the proton beam traveling distance, $\Delta$, 48 through the target volume is uniform from the point at which the proton beam enters the target volume, $T_s$, 46 to the point where the proton beam reaches the far extreme of the target volume, $T_e$, 50. The asymptotic value can be assumed to depend on the distance, $\Delta$, 48 the ray travels inside the target volume. Further, according to the dose curve 42, no energy is released by the proton beam beyond the far extreme of the target volume, $T_e$, 50.

For example, in an embodiment, the dose prediction module 14 applies the following definition of a proton beam geometry-expected-dose (GED) metric representing the dose contribution from a proton beam with respect to a location, or voxel:

$$Gx = \begin{cases} \Delta + (d-\Delta)e^{-a\sqrt{T_s-x}+b} & x < T_s \\ d & T_s < x < T_e \\ 0 & T_e < x \end{cases}$$

where G x is the single proton field contribution to the geometry-expected dose, x is the distance from the proton beam source, the target volume starts at distance $T_s$ and ends at distance $T_e$, $\Delta$ is the distance the ray travels in the target volume, d is the prescription dose level from the specified field to the target, and parameters a and b are phenomenological coefficients. In an embodiment, distances are measured in units that correspond to the energy release of a proton beam far before the Brachy peak.

The coefficients, a and b, are exponential parameters that depend on the selected dimensions of the proton therapy setup. In an embodiment, the coefficients, a and b, may be determined using statistical analysis of patient geometry and dose information from historical proton beam treatment plans. For example, depending on the selected dimensions, the value of the coefficient a may be approximately in the range of 0.4 to 0.8, and the value of the coefficient b may be approximately in the range of 2.75 to 12. In one embodiment the empirically determined coefficients, a=0.6, and b=5, have produced useful predictions.

In an embodiment, the dose prediction module 14 permits interactive definition and fine-tuning of the target volume to be treated while providing an immediate estimate of the achievable plan quality. The quality can be described, for example, by predicting the dose-volume histograms (DVHs) that would be achieved for a specific target volume. The dose prediction module 14 can facilitate decisions, for example, regarding the clinical tradeoff between the size of spatial region to be irradiated and sparing of critical organs.

In another embodiment, the dose prediction module 14 permits interactive definition and modification of the proton beam field geometry while providing an immediate estimate of the achievable plan quality. Thus, independent dose optimization would not be required for each candidate target volume and field geometry. Further, in an embodiment, the proton beam dose distribution is evaluated with respect to multiple target volumes, for example, adding weighted contributions, or fractionations, corresponding to the various modified distances from an OAR to multiple target volumes with different dose levels.

In various embodiments, the GED metrics are used in dose-volume histogram (DVH) estimation, fluence estimation, or three-dimensional dose estimation. In an embodiment, estimated dose distributions based on GED metrics are compared with corresponding proton beam dose distributions actually achieved in clinical treatments to tune an actual knowledge model.

The knowledge assimilation module 16 extracts major dosimetric features from existing proton therapy datasets representing the actual historical patient population. In knowledge-based dose prediction, information gleaned from actual historical plans is used to estimate the achievable proton dose distribution regarding a new patient. For example, patient geometry and dose information of multiple historical proton beam treatment plans is distilled into a prediction model that can be used for proton beam therapy dose prediction without storing all of the information from the original set of plans.

The knowledge base 18 stores the existing proton therapy datasets representing a historical population of actual patient anatomical and achieved dose information. Thus, the proton beam dose distribution planning tool 10 can create proton-specific DVH estimation models based on a set of existing proton plans. The systems described herein can offer advantages such as evaluating plans with different proton field geometries, evaluating plans with multiple target volumes with differing dose levels, and analyzing the effect of target volume shape on dose distribution.

An embodiment of the present invention correlates achieved dose distributions in actual historical patient proton therapy treatment plans to specific underlying patient anatomy and stores the resultant correlation information in the knowledge base 18. The correlation information in the knowledge base 18 is accessed in order to predict three-dimensional dose distribution for new patients based on patient anatomy. Thus, the proton beam dose distribution planning tool 10 correlates proton beam dose distributions achieved in actual patients in radiotherapy treatments with the underlying patient anatomy, or geometry.

Figure 4:
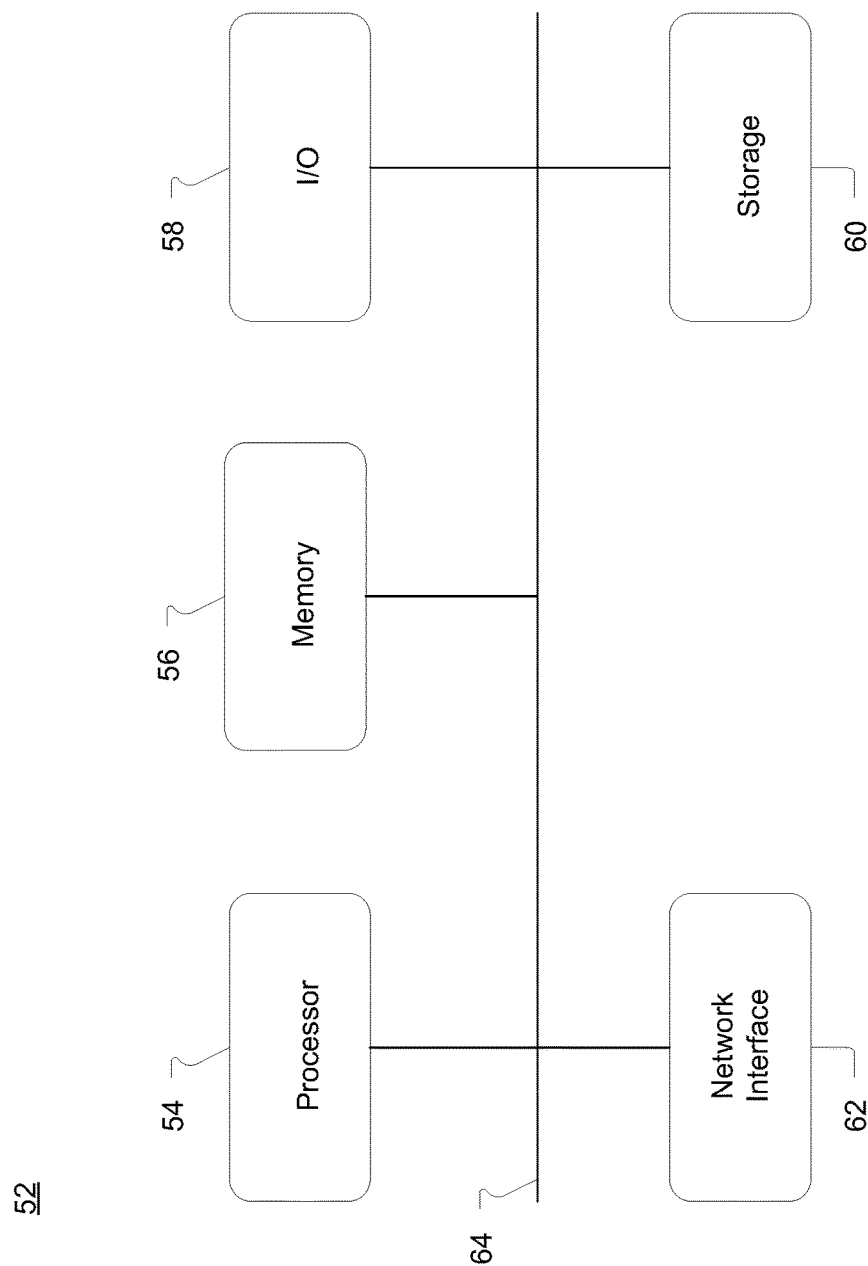
FIG. 4 is a schematic view depicting an exemplary general computing system that can implement the proton beam dose distribution planning tool of FIG. 1.

As illustrated in FIG. 4, an exemplary general computing device 52 that can be employed in the proton beam dose distribution planning tool 10 of FIG. 1 includes a processor 54, a memory 56, an input/output device (I/O) 58 storage 60 and a network interface 62. The various components of the computing device 52 are coupled by a local data link 64, which in various embodiments incorporates, for example, an address bus, a data bus, a serial bus, a parallel bus, or any combination of these.

The computing device 52 communicates information to and requests input from the user or other devices by way of the I/O 58, which in various embodiments incorporates, for example, an interactive, menu-driven, visual display-based user interface, or graphical user interface (GUI), a pointing device, such as a, with which the user may interactively input information using direct manipulation of the GUI.

The computing device 52 can be coupled to a communication network by way of the network interface 62, which in various embodiments incorporates, for example, any combination of devices—as well as any associated software or firmware—configured to couple processor-based systems, including modems, access points, network interface cards, LAN or WAN interfaces, wireless or optical interfaces and the like, along with any associated transmission protocols, as may be desired or required by the design.

The computing device 52 can be used, for example, to implement the functions of the components of the proton beam dose distribution planning tool 10 of FIG. 1. In various embodiments, the computing device 52 can include, for example, a server, a controller, a workstation, a mainframe computer, personal computer (PC), a note pad, a computing tablet, a personal digital assistant (PDA), a smart phone, a wearable device, or the like. Programming code, such as source code, object code or executable code, stored on a computer-readable medium, such as the storage 60 or a peripheral storage component coupled to the computing device 52, can be loaded into the memory 56 and executed by the processor 54 in order to perform the functions of the proton beam dose distribution planning tool 10.

Figure 5:
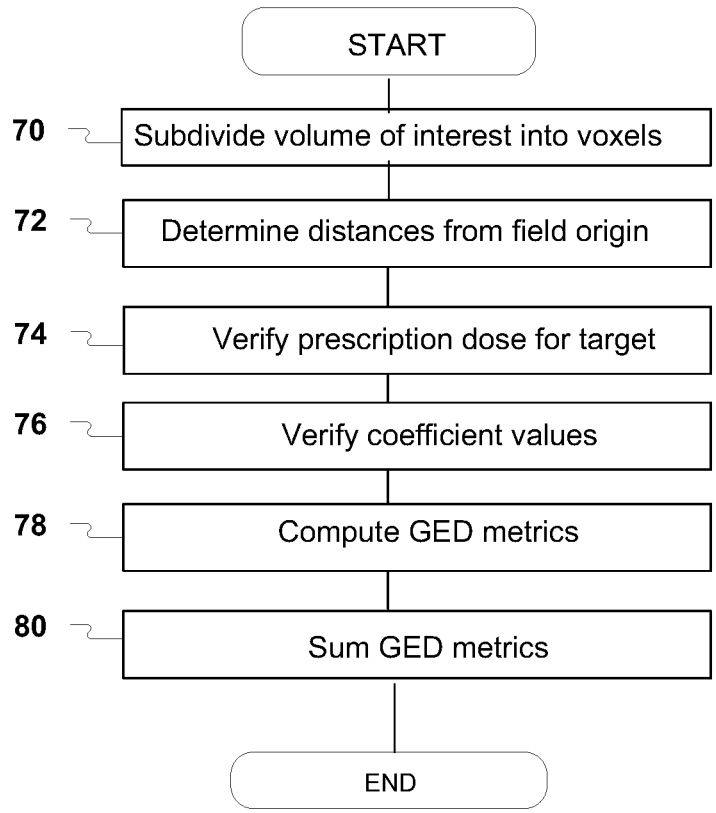
FIG. 5 is a flowchart representing an exemplary method of estimating the dose distribution of a proton beam in accordance with an embodiment of the present invention.

Referring now to FIG. 5, an exemplary process flow is illustrated that may be performed, for example, by the proton beam dose distribution planning tool 10 of FIG. 1 to implement an embodiment of the method described in this disclosure for employing a proton beam geometry-expected-dose (GED) to develop and evaluate patient-specific proton therapy treatment plans. The process begins at block 70, where a volume of interest, such as a target volume or an organ at risk (OAR), is subdivided into a group of voxels, for example, equal-sized, three-dimensional units, as described above.

As further described above, in block 72, the distance from the planned proton beam field origin to each voxel is determined. The prescription dose for the target is ascertained, in block 74, and the value of one or more phenomenological coefficients that depend on the selected dimensions of the proton therapy setup are ascertained, in block 76.

In block 78, as explained above, geometry-based expected dose (GED) metrics are computed for all voxels with respect to each planned proton field. In block 80, the GED metrics are summed for all voxels in the volume of interest with respect to each field. The summation of the GED metrics provides an estimation of the total dose received by the volume of interest in the planned proton beam therapy.

Aspects of this disclosure are described herein with reference to flowchart illustrations or block diagrams, in which each block or any combination of blocks can be implemented by computer program instructions. The instructions may be provided to a processor of a general purpose computer, special purpose computer, or other programmable data processing apparatus to effectuate a machine or article of manufacture, and when executed by the processor the instructions create means for implementing the functions, acts or events specified in each block or combination of blocks in the diagrams.

In this regard, each block in the flowchart or block diagrams may correspond to a module, segment, or portion of code that includes one or more executable instructions for implementing the specified logical function(s). It should also be noted that, in some alternative implementations, the functionality associated with any block may occur out of the order noted in the figures. For example, two blocks shown in succession may, in fact, be executed substantially concurrently, or blocks may sometimes be executed in reverse order.

A person of ordinary skill in the art will appreciate that aspects of this disclosure may be embodied as a device, system, method or computer program product. Accordingly, aspects of this disclosure, generally referred to herein as circuits, modules, components or systems, or the like, may be embodied in hardware, in software (including firmware, resident software, micro-code, etc.), or in any combination of software and hardware, including computer program products embodied in a computer-readable medium having computer-readable program code embodied thereon.

It will be understood that various modifications may be made. For example, useful results still could be achieved if steps of the disclosed techniques were performed in a different order, and/or if components in the disclosed systems were combined in a different manner and/or replaced or supplemented by other components. Accordingly, other implementations are within the scope of the following claims.

What is claimed is:

1. A method of estimating a dose from a proton therapy plan, said method comprising:
    subdividing a representation of a volume of interest into a plurality of voxels;
    assigning metrics to the plurality of voxels; and
    summing a plurality of discrete contributions corresponding to the plurality of voxels to yield an estimated dose corresponding to the volume of interest, wherein the plurality of discrete contributions include the metrics.

2. The method described in claim 1, wherein said metrics are based on at least one of: a volume of the volume of interest; a volume of an organ at risk; a portion of the organ at risk that is located outside of the plurality of proton fields; a number and an orientation of the plurality of proton fields; a geometry of the plurality of proton fields; a tissue density; a prescription dose; an energy deposition characteristic; and an energy dispersion characteristic.

3. The method described in claim 1, wherein said assigning metrics to the plurality of voxels comprises computing a geometrically-expectable dose distribution for the voxels with respect to a plurality of proton fields for delivering the dose.

4. The method described in claim 3, wherein said geometrically-expectable dose distribution is based on a number of voxels of the plurality of voxels that are crossed by the plurality of proton fields before reaching the volume of interest.

5. The method described in claim 3, wherein said geometrically-expectable dose distribution comprises a patient geometry metric, and wherein said method further comprises determining a beam geometry for delivering the dose based on the patient geometry metric.

6. The method described in claim 5, wherein said beam geometry comprises a beam orientation that satisfies a constraint associated with the volume of interest.

7. The method described in claim 1, wherein the volume of interest comprises an organ at risk.

8. A system for estimating a dose from a proton therapy plan, said system comprising:
    a memory that stores machine instructions; and
    a processor coupled to the memory that executes the machine instructions to:
        subdivide a representation of a volume of interest into a plurality of voxels;
        assign metrics to the plurality of voxels; and
        sum a plurality of discrete contributions corresponding to the plurality of voxels to yield an estimated dose corresponding to the volume of interest, wherein the plurality of discrete contributions include the metrics.

9. The method described in claim 8, wherein said metrics are based on at least one of: a volume of the volume of interest; a volume of an organ at risk; a portion of the organ at risk that is located outside of the plurality of proton fields; a number and an orientation of the plurality of proton fields; a geometry of the plurality of proton fields; a tissue density; a prescription dose; an energy deposition characteristic; and an energy dispersion characteristic.

10. The method described in claim 8, wherein said assigning metrics to the plurality of voxels comprises computing a geometrically-expectable dose distribution for the voxels with respect to a plurality of proton fields for delivering the dose.

11. The method described in claim 10, wherein said geometrically-expectable dose distribution is based on a number of voxels of the plurality of voxels that are crossed by the plurality of proton fields before reaching the volume of interest.

12. The method described in claim 10, wherein said geometrically-expectable dose distribution comprises a patient geometry metric, and wherein said method further comprises determining a beam geometry for delivering the dose based on the patient geometry metric.

13. The method described in claim 12, wherein said beam geometry comprises a beam orientation that satisfies a constraint associated with the volume of interest.

14. The method described in claim 13, wherein the volume of interest comprises an organ at risk.

15. A non-transitory, computer-readable storage medium encoded with instructions that are executed by a processor to perform a method for estimating a dose from a proton therapy plan, said method comprising:
subdividing a representation of a volume of interest into a plurality of voxels;
assigning metrics to the plurality of voxels; and
summing a plurality of discrete contributions corresponding to the plurality of voxels to yield an estimated dose corresponding to the volume of interest, wherein the plurality of discrete contributions include the metrics.

16. The computer-readable storage medium described in claim 15, wherein said metrics are based on at least one of: a volume of the volume of interest; a volume of an organ at risk; a portion of the organ at risk that is located outside of the plurality of proton fields; a number and an orientation of the plurality of proton fields; a geometry of the plurality of proton fields; a tissue density; a prescription dose; an energy deposition characteristic; and an energy dispersion characteristic.

17. The computer-readable storage medium described in claim 15, wherein said assigning metrics to the plurality of voxels comprises computing a geometrically-expectable dose distribution for the voxels with respect to a plurality of proton fields for delivering the dose.

18. The computer-readable storage medium described in claim 17, wherein said geometrically-expectable dose distribution is based on a number of voxels of the plurality of voxels that are crossed by the plurality of proton fields before reaching the volume of interest.

19. The computer-readable storage medium described in claim 17, wherein said geometrically-expectable dose distribution comprises a patient geometry metric, and wherein said method further comprises determining a beam geometry for delivering the dose based on the patient geometry metric.

20. The computer-readable storage medium described in claim 19, wherein said beam geometry comprises a beam orientation that satisfies a constraint associated with the volume of interest.

* * * * *